United States Patent [19]

Barchas et al.

[11] Patent Number: 4,978,669
[45] Date of Patent: Dec. 18, 1990

[54] METHOD OF SUPPRESSING APPETITE BY ADMINISTRATION OF TETRAHYDRO-BETA-CARBOLINE DERIVATIVES

[75] Inventors: Jack D. Barchas, Stanford; Glen R. Elliott, Sunnyvale; Peter I. Adriaenssens, Palo Alto; Robert S. Bitner, Mountain View; Stephen S. Bowersox, Menlo Park; Laszlo Nadasdi, San Francisco, all of Calif.

[73] Assignee: Neurex Corporation, Menlo Park, Calif.

[21] Appl. No.: 363,504

[22] Filed: Jun. 8, 1989

[51] Int. Cl.$^5$ ............................................. A61K 31/44
[52] U.S. Cl. ..................................... 514/292; 514/909
[58] Field of Search ................. 514/292, 909; 546/85, 546/86

[56] References Cited

U.S. PATENT DOCUMENTS 3,294,809 12/1966 Shaveh, Jr. ........................... 546/86
4,336,260 6/1982 Payne et al. .

FOREIGN PATENT DOCUMENTS 3430389 2/1986 Fed. Rep. of Germany ...... 540/548
1183219 3/1970 United Kingdom .

OTHER PUBLICATIONS

Glassman et al., Science, vol. 226, 1984, pp. 864–866.
Airaksinen et al., Med. Biol., 1981, 59:190–211.
Huttunen et al., Pharmacol. Biochem. & Behav., (1986), 24:1773–1778.
Rommelspacher et al., Naunyn–Schiedeberg's Arch. Pharmacol., (1977), 298:83–91.
Cooper, Eur. J. Pharmacol., (1986), 120:257–265.
Skonick et al., "Beta-Carbolines and Tetrahydroisquinolines", A. R. Liss, editor, New York, (1982), pp. 233–252.
Robertson et al., Eur. J. Pharmacol., (1981), 76:281–284.
Greiner et al., Naunyn–Schmiedberg's Arch. Pharmacol., (1983), 322:140–146.
Cain et al., J. Med. Chem., (1982), 25(9):1981–1091.

Koho, Chem. Abstracts, (1981), 95:705, Abstract No. 115508a.
Koho, Chem. Abstracts, (1984), 101:655, Abstract No. 110890b.
Ikuo et al., Chem. Abstracts, (1986), 105:726, Abstract No. 191049s.
Haffer et al., Chem. Abstracts, (1987), 106:604.

(List continued on next page.)

Primary Examiner—Mukund J. Shah
Assistant Examiner—E. C. Ward
Attorney, Agent, or Firm—Peter J. Dehlinger

[57] ABSTRACT

Compounds of formula I are useful for suppressing appetite, for altering macronutrient preferences, for suppressing obsessive-compulsive behavior, and for inhibiting cravings and substance abuse:

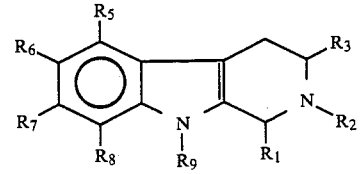

(I)

wherein
  $R_1$ and $R_3$ are each independently H, hydroxy-alkyl, alpha-cyanoalkyl, $SO_3H$, $SO_2NH_2$, or $C(O)R$, where R is OH, $NH_2$, lower alkoxy, benzyloxy, or aliphatic amino acyl;
  $R_2$ and $R_9$ are each independently H, lower alkyl, benzyl, succinyl, or $C(O)R_4$, where $R_4$ is H, lower alkyl, hydrocarboxy-lower alkylene, or lower alkoxycarboxy-lower alkylene; and
  $R_5$, $R_6$, $R_7$, and $R_8$ are each independently H, halo, lower alkyl, hydroxy, lower alkoxy, or two adjacent radicals form methylenedioxy or ethylenedioxy;
  with the proviso that $R_1$, $R_2$, $R_3$, $R_5$, $R_6$, $R_7$, $R_8$, and $R_9$ are not simultaneously H.

2 Claims, 2 Drawing Sheets

OTHER PUBLICATIONS

Shavel, *Chem. Abstracts*, (1967), 66:7128, Abstract No. 75985w.

Ikuo et al., *Chem. Abstracts*, (1985), 103:711 Abstract No. 160488p.

Biere, *Chem. Abstracts*, (1984), 101:643, Abstract No. 72711j.

Koho, *Chem. Abstracts*, (1983), 98:639, Abstract No. 126057r.

Koho, *Chem. Abstracts*, (1982), 96:771, Abstract No. 218092k.

Neef et al., *Chem. Abstracts*, (1983), 98:510, Abstract No. 16663c.

Langbein et al., *Chem. Abstracts*, (1972), 77:399, Abstract No. 126602f.

METHOD OF SUPPRESSING APPETITE BY ADMINISTRATION OF TETRAHYDRO-BETA-CARBOLINE DERIVATIVES

DESCRIPTION

1. Technical Field

This invention relates to pharmacologic control of appetite More specifically, this invention relates to methods for suppressing feeding behavior and modifying macronutrient preference, and compounds useful therefore.

2. Background of the Invention

The high prevalence of obesity in the United States attests to the general failure of existing medical treatments to adequately manage the problem. The limited efficacy of existing anorectic agents when measured against possible risk factors inherent in their use currently precludes them as treatments of choice for the management of obesity However, there is a growing awareness among both patients and the medical community that obesity is a disease that requires aggressive medical intervention. Thus, new anti-obesity agents with significantly improved performance characteristics are likely to be well-received in the future.

Although the nosology of obesity and related eating disorders is not currently well defined, with its development and broadening acceptance grows the need to design safe and effective pharmacotherapies. The most commonly used weight control agents available without prescription are generally adrenergic stimulants such as phenylpropanolamine and phenethylamine derivatives. Although effective appetite inhibitors, adrenergic agents produce numerous untoward side effects, such as nervousness, irritability, insomnia, dizziness, tachycardia, palpitations, hypertension, and the like. These side effects may be severe enough to require cessation of treatment. Kopf, DE 3,430,389, disclosed weight-reduction by administering a combination of an adrenergic agent with a benzodiazepine sedative. The actual safety of such adrenergic agents is questionable, particularly in view of the 20–30% of the U.S. population suffering from hypertension. Although the non-stimulant anorectic agent fenfluramine is devoid of the psychomotor stimulant properties and abuse potential seen with stimulant-like compounds (e.g., amphetamine), it often has an inadequate clinical efficacy, and patients receiving the drug often complain of drowsiness and headache. Thus, it is apparent that none of the current anti-obesity pharmacotherapies available are particularly satisfactory.

The present invention relates to a novel use for certain derivatives of 1,2,3,4-tetrahydro-beta-carboline (1,2,3,4-tetrahydro-9H-pyrido[3,4-b]indole). The compound possesses the following structural formula:

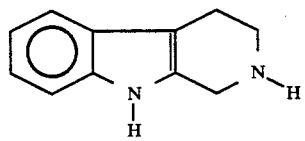

Tetrahydro-beta-carboline (THBC) has a variety of pharmacological actions and has been variously evaluated as a cholinesterase inhibitor, sedative/hypnotic, analgesic, and psychotomimetic. It competes with low affinity for brain tryptamine, imipramine, 5-hydroxy-tryptamine (5-HT), and spiperone binding sites, enhances depolarization-induced 5-HT efflux from brain slices, and weakly inhibits 5-HT uptake in brain synaptosomes and 5-HT oxidative deamination. It occurs naturally in mammalian brain tissue When THBC is administered parenterally to laboratory animals, it suppresses locomotion, exploratory activity, and conflict behavior, impairs performance on operantly conditioned learning and memory tasks, reduces seizure susceptibility, prolongs barbiturate sedation, and antagonizes specific drug-induced stereotypies. When given in high doses, THBC induces a characteristic behavioral syndrome characterized by hyperactivity, forepaw treading, body weaving, and circling (Airaksinen et al, *Med Biol* (1981) 59:190–211). Paradoxically, THBC has been reported to reduce motor activity, induce apparent anxiety, and increase voluntary ethanol consumption when administered intraventricularly to rats (P. Huttunen et al, *Pharmacol Biochem & Behav* (1986) 24:1733–38). Atkinson, GB 1,183,219 disclosed its use as an analgesic.

Physiological actions of THBC include effects on endocrine secretory patterns and body temperature. Systemic administration in rodents produces a dose-dependent elevation of plasma prolactin levels, decreased serum luteinizing hormone levels, and elevated plasma corticosterone. THBC elicits significant hypothermia when administered to rats parenterally in doses of 6.25 mg/Kg or greater (H. Rommelspacher et al, *Naunyn-Schmiedeberg's Arch Pharmacol* (1977) 298:83–91).

It is also known that daily oral administration of THBC produces temporary dose-related decrements in food and fluid intake in rats Animals that receive average daily amounts of THBC in excess of 49 mg/Kg show significant reductions in food intake after two consecutive days of treatment; tolerance develops, and food consumption returns to normal by the twelfth treatment day. Smaller daily doses (less than 30 mg/Kg) do not significantly alter appetite (Rommelspacher; Airaksinen et al, *Med Biol* (1981) 59:190–211). It is noteworthy that in Rommelspacher,s report, 6 out of the 24 animals receiving 49 mg/Kg/day or greater died.

Payne et al, U.S. Pat. No. 4,336,260 disclosed the use of 1-aryl-3-carboxylic acid THBC derivatives as antidepressants.

S. Cooper, *Eur J Pharmacol* (1986) 120:257–65 disclosed that three fully-unsaturated beta-carboline derivatives exhibit hyperphagic activity, while another beta-carboline derivative exhibits anorectic activity. The hyperphagic derivatives were ethyl 6-benzyloxy-4-methoxymethyl-beta-carboline-3-carboxylate, ethyl 5-benzyloxy-4-methoxymethyl-beta-carboline-3-carboxylate, and ethyl 5-isopropoxy-4-methyl-beta-carboline-3-carboxylate. The anorectic derivative was betacarboline-3-carboxylic acid methyl amide (FG 7142). When injected intraperitoneally at 10.0 mg/Kg, FG 7142 reduced food consumption by partially sated rats to 30% of control.

P. Skolnick et al, in "Beta-Carbolines and Tetrahydroisoquinolines" (Alan R. Liss, 1982, N.Y.) pp. 233–52 disclosed that certain carboxy-ester beta-carboline derivatives bind with high affinity to benzodiazepine receptors. This binding may account for the ability of these compounds to antagonize the anticonvulsant, anxiolytic, and sedative properties of benzodiazepine drugs. However, saturated derivatives such as 3-carbomethoxy-1,2,3,4-tetrahydro-beta-carboline bind with very low affinity (Skolnick, supra; H. A. Robertson et al, *Eur J Pharmacol* (1981) 76:281-84).

DISCLOSURE OF THE INVENTION

We have now found that certain derivatives of THBC when administered to warm-blooded animals partially or fully suppress feeding behavior. The compounds of the invention are effective at doses lower than those required by other THBC analogs, and exhibit fewer and less severe side effects. These compounds are also useful for altering macronutrient preferences (e.g., by reducing appetite for carbohydrates), and for treatment of substance abuse. Compounds of the invention exhibit very low affinity for 5-HT receptors, 5-HT uptake sites, and benzodiazepine receptors. Thus, we currently believe that the compounds of the invention act by a mechanism different from that of related unsaturated compounds.

One aspect of the invention is the method of suppressing feeding behavior in a mammal by administering an effective amount of a compound of formula I:

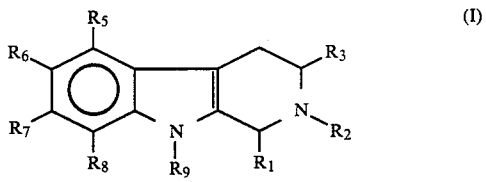

where $R_1$ and $R_3$ are each independently H, hydroxyalkyl, alpha-cyanoalkyl, $SO_3H$, $SO_2NH_2$, or $C(O)R$, where R is OH, $NH_2$, lower alkoxy, benzyloxy, or aliphatic amino acyl; $R_2$ and $R_9$ are each independently H, lower alkyl, benzyl, succinyl, or $C(O)R_4$, where $R_4$ is H, lower alkyl, hydrocarboxy-lower alkylene, or lower alkoxycarboxy-lower alkylene; and $R_5$, $R_6$, $R_7$, and $R_8$ are each independently H, halo, lower alkyl, hydroxy, lower alkoxy, or two adjacent radicals form methylenedioxy or ethylenedioxy; with the proviso that $R_1$, $R_2$, $R_3$, $R_5$, $R_6$, $R_7$, $R_8$, and $R_9$ are not simultaneously H.

Presently preferred compounds are those wherein either $R_1$ or $R_3$ is C(O)R and R is OH, alkoxy or benzyloxy, particularly where R is benzyloxy. Another presently preferred compound is that wherein $R_2$ is $C(O)R_4$ and $R_4$ is methyl, and $R_1$ and $R_3$ are each H.

Another aspect of the invention is a composition useful for suppression of feeding behavior in a mammal, which comprises a pharmaceutically acceptable excipient in combination with an effective amount of a compound of formula I.

Another aspect of the invention is a method for partially suppressing appetite in a mammal, by administering a compound of formula I in which $R_{5-9}$ are all H to a mammal in need thereof Another aspect of the invention is a composition for partially suppressing appetite in a mammal.

Another aspect of the invention is a method and composition for altering macronutrient preference in a mammal by administering a compound of formula I.

Another aspect of the invention is a method and composition for suppressing substance cravings in a mammal by administering a compound of formula I.

Another aspect of the invention is a method and composition for suppressing obsessive-compulsive behavior in a mammal by administering a compound of formula I.

BRIEF DESCRIPTION OF THE DRAWINGS

FIG. 1 compares D,L-3-carboxy-THBC ($R_3$=COOH) with THBC.

FIG. 2 compares D,L-3-carbobenzyloxy-THBC ($R_3$=COOCH$_2$C$_6$H$_5$) with THBC.

FIG. 3 compares 2-acetyl-THBC ($R_2$=C(O)CH$_3$) with THBC.

FIG. 4 compares D,L-1-carboxy-THBC ($R_1$=COOH) with THBC.

MODES OF CARRYING OUT THE INVENTION

A. Definitions

Figure 1:
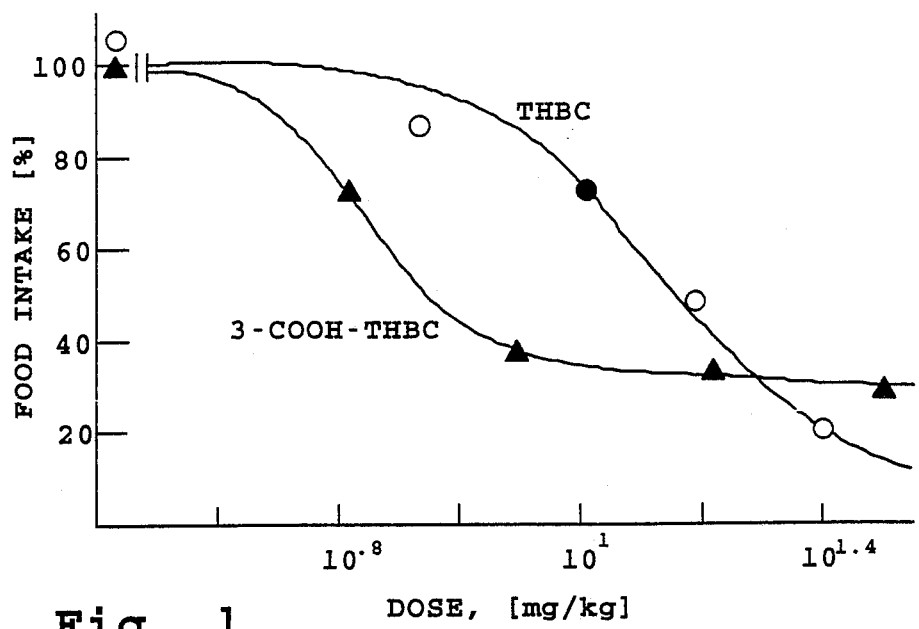
FIGS. 1-4 demonstrate partial suppression of feeding behavior obtained with compounds of the invention, as illustrated in Example 3.

The phrase "compound of formula I" as used herein refers to compounds having the following structural formula, and their pharmaceutically acceptable salts:

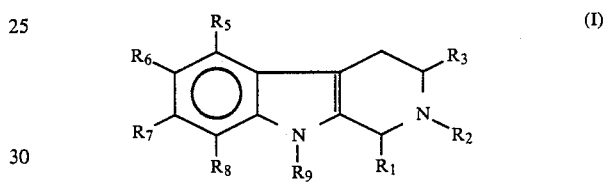

where $R_1$ and $R_3$ are each independently H, hydroxyalkyl, alpha-cyanoalkyl, $SO_3H$, $SO_3NH_2$, or $C(O)R$, where R is OH, $NH_2$, lower alkoxy, benzyloxy, or aliphatic amino acyl; $R_2$ and $R_9$ are each independently H, lower alkyl, benzyl, succinyl, or $C(O)R_4$, where $R_4$ is H, lower alkyl, hydrocarboxy-lower alkylene, or lower alkoxycarboxy-lower alkylene; and $R_5$, $R_6$, $R_7$, and $R_8$ are each independently H, halo, lower alkyl, hydroxy, lower alkoxy, or two adjacent radicals form methylenedioxy or ethylenedioxy; with the proviso that $R_1$, $R_2$, $R_3$, $R_5$, $R_6$, $R_7$, $R_8$, and $R_9$ are not simultaneously H.

The term "lower alkyl" as used herein refers to saturated monovalent hydrocarbon radicals having from 1 to 6 carbon atoms, for example, methyl, ethyl, propyl, isopropyl, butyl, hexyl, and the like.

The term "lower alkoxy" refers to radicals of the form -OR, where R is lower alkyl as defined above. Suitable lower alkoxy radicals include methoxy, ethoxy, propoxy, and the like.

The term "hydroxy-alkyl" refers to a lower alkyl group wherein one hydrogen atom is replaced with a hydroxy radical, for example, hydroxymethyl, 2-hydroxyethyl, 1-hydroxyethyl, 3-hydroxypropyl, 2-methyl-2-hydroxypropyl, and the like.

The term "alpha-cyanoalkyl" refers to a radical of the form -CH(CN)R, where R is lower alkyl as defined above. Exemplary alpha-cyanoalkyl radicals include without limitation cyanomethyl, 1-cyanoethyl, 1-cyanopropyl, 1-cyano-3-methylbutyl, 1-cyanohexyl, and the like.

The term "halo" means fluoro, chloro, bromo, or iodo.

The terms "methylenedioxy" and "ethylenedioxy" refer to divalent radicals of the formula —O—CH—O— and —O—CH$_2$CH$_2$O—, respectively. When two adjacent radicals are methylenedioxy or ethylenedioxy, a five or six-membered ring is formed. "Two adjacent radicals" means $R_5$ and $R_6$, $R_6$ and $R_7$, or $R_7$ and $R_8$.

The term "aliphatic amino acyl" refers to radicals derived from commonly-available amino acids which are fully saturated. Specifically, aliphatic amino acyl refers to glycyl, alanyl, leucyl, isoleucyl, valyl, and norleucyl.

The term "hydrocarboxy-lower alkylene" refers to radicals of the form $-(CH_2)_nCOOH$, where n is an integer from 0 to 6. Thus, where $R_2$ is $C(O)R_4$ and $R_4$ is hydrocarboxy-lower alkylene, suitable radicals will include oxalyl, malonyl, succinyl, glutaryl, and adipoyl.

The term "alkoxycarboxy-lower alkylene" refers to radicals of the form $-(CH_2)_nCOOR$, where n is an integer from 0 to 6 and R is lower alkyl as defined above. Thus, where $R_2$ is $C(O)R_4$ and $R_4$ is alkoxycarboxy-lower alkylene, suitable radicals will include methyloxalyl, methylmalonyl, ethylmalonyl, propylsuccinyl, and the like.

The term "feeding behavior" as used herein refers to food intake and associated behavior. "Partial suppression" of feeding behavior refers to reduction of feeding behavior to a level between about 20% and about 70% of control behavior.

The term "effective amount" refers to the amount of a selected compound of formula I which is necessary to cause suppression of feeding behavior. The precise amount required will vary depending upon the particular compound selected, the age and weight of the subject, route of administration, and so forth, but may easily be determined by routine experimentation. Suitable experiments are described in the Examples. In general, however, an effective amount will range from about 1 mg/Kg to about 100 mg/Kg, preferably about 2 mg/Kg to about 30 mg/Kg, more preferably about 4-12 mg/Kg. Partial suppression of feeding behavior is effected by administration of similar amounts of the appropriate compounds of formula I (generally compounds of formula I in which $R_{5-9}$ are all H).

The term "appetite-altering amount" refers to the dosage of compound required to alter the appetite for carbohydrates experienced by the subject animal, i.e., to alter the subjects macronutrient preferences. The term "appetite-altering amount" also applies to the quantity required to effect a change in chemical dependency; in other words, a therapeutic amount in the treatment of e.g., alcohol, tobacco, narcotic or opiate addiction. The precise appetite-altering amount required will vary with the particular compounds employed, the species, age and condition of the subject to be treated. However, the amount may be determined by one of ordinary skill in the art with only routine experimentation, following methods known in the art, and disclosed below. In general, an appetite-altering amount will be roughly one half to one tenth the effective amount described above. Thus, the appetite-altering amount will range from about 0.01 to about 10 mg/Kg body weight, preferably about 0.5-5 mg/Kg, and most preferably about 1 mg/Kg.

The term "drugs of abuse" refers to those compounds other than alcohol and tobacco which present the potential for addiction and chemical dependency, such as opiates (e.g., heroin, morphine, etc.), alkaloids (e.g., cocaine), marijuana, peyote, and the like.

The term "obsessive-compulsive behavior" refers to actions and/or thoughts which a mammal experiences on a frequent or repetitive basis with little or no volitional control. "Habits" are a very mild, subclinical form of such behavior, but are generally not considered obsessive-compulsive behavior until they become socially debilitating. Subjects exhibiting obsessive-compulsive behaviors are generally aware of their behavior and its abnormality, but are unable to consciously modify their behavior. Examples of obsessive-compulsive behavior include compulsive hand-washing, washing, obsessive counting, continual hand-wringing, and the like. A "behavior modifying amount" refers to the amount of a compound of formula I which is necessary to assist a subject in regaining volitional control, so that an obsessive-compulsive behavior may be consciously suppressed. The behavior modifying amount will generally be similar to the amount needed for appetite suppression.

The term "pharmaceutically acceptable" refers to a compound, salt, or excipient which is not unacceptably toxic to the subject to which it is administered. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, and the like. Pharmaceutically acceptable excipients are described at length by E. W. Martin, in "Remington's Pharmaceutical Sciences" (Mack Pub. Co.).

B. General Method

Compounds of the invention may be prepared by a variety of methods known to those of ordinary skill in the art (M. Cain et al, *J Med Chem* (1982) 25:1081-91). Three exemplary methods are presented below as Schemes I-III.

In Scheme I, a substituted tryptamine is cyclized by reaction with an appropriate aldehyde under acid catalysis to form a tetrahydro-beta-carboline derivative of formula I (where $R_2$ is H). This product may be $N^2$-acylated in pyridine, with or without a co-solvent, to provide compounds of formula I wherein $R_2$ is other than hydrogen.

In Scheme II, tryptamine or a substituted tryptamine is cyclized by reaction with an appropriate ketoacid under acid catalysis to form a tricyclic carboxy product. This product may then be decarboxylated under acid catalysis to provide a tetrahydro-beta-carboline derivative of formula I (where $R_2$ is H). This product may be $N^2$-acylated in pyridine, with or without a co-solvent, to provide compounds of formula I wherein $R_2$ is other than hydrogen.

In Scheme III, the $N^2$-acylated product of Scheme I or II above is alkylated at the $N^9$ position in the presence of sodium hydride in dimethyl formamide to provide compounds of formula I in which $R_9$ is other than hydrogen. These $N^2$-acyl-$N^9$-alkyl derivatives may be deacylated by refluxing with alkali to provide compounds of formula I in which $R_9$ is other than H and $R_2$ is H.

Scheme I

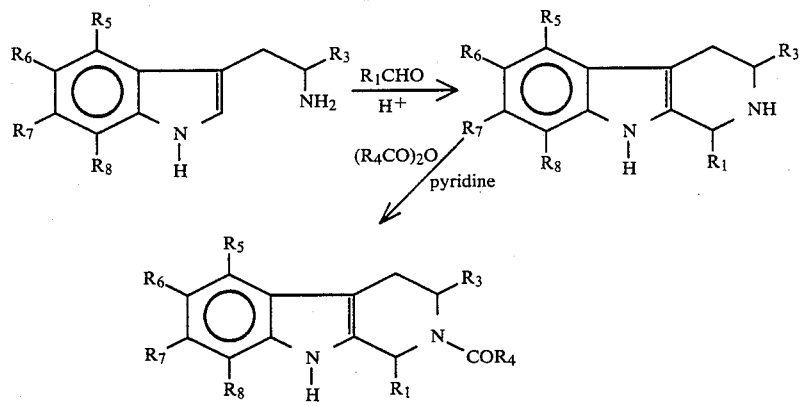

Scheme II

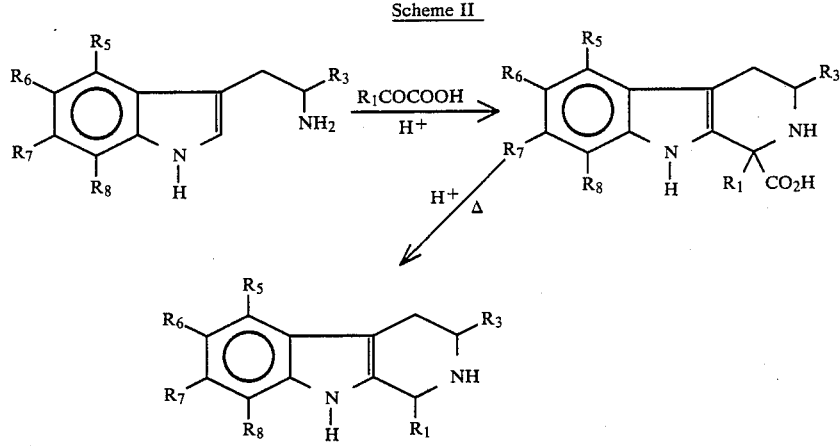

Scheme III

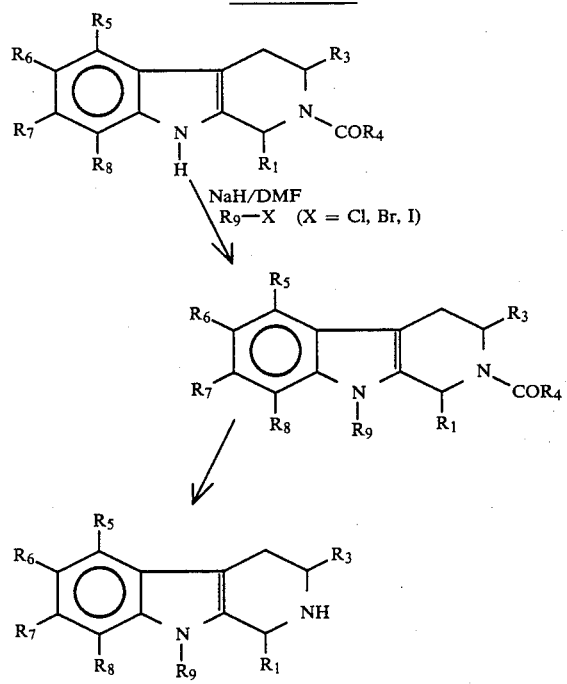

Pharmaceutical compositions containing compounds of formula I, preferably as acid addition salts, may contain one or more pharmaceutical carriers. When the carrier serves as a diluent, it may be solid, semisolid, or liquid material acting as a vehicle, excipient, or medium for the active ingredient. Pharmaceutical unit dosage forms may be prepared for administration by any of several routes including, but not limited to, oral and parenteral (especially by intramuscular and intravenous injection, or by subcutaneous implant or transdermal administration). Representative of such forms are tablets, soft and hard gelatin capsules, powders, lozenges, chewing gums, emulsions, suspensions, syrups, solutions, sterile injectable solutions, and sterile packaged powders. Compositions containing compounds of formula I may be formulated by procedures known in the art so as to provide rapid, sustained, or delayed release of any or all of the compounds after administration.

Solid pharmaceutical excipients such as magnesium stearate, calcium carbonate, silica, starch, sugar, talc, and the like may be used with other conventional pharmaceutical adjuvants including fillers, lubricants, wetting agents, preserving agents, disintegrating agents, flavoring agents, and binders such as gelatin, gum arabic, cellulose, methylcellulose, and the like, to form admixtures which may be used as such or may be tabulated, encapsulated, or prepared in other suitable forms as noted above. The preferred liquid diluent is physiologically normal saline. A general description of formulation is given in "Remington's Pharmaceutical Sciences" (Mack Pub. Co.).

Compounds of formula I produce significant, long-lasting reduction in feeding behavior when administered to mammals within 8 hours prior to meal presentation. Administration is preferably by oral dosage, but may be by transdermal application, intranasal spray, bronchial inhalation, suppository, parenteral injection (e.g., intramuscular or intravenous injection), and the like. At other doses, compounds of formula I are useful for suppressing obsessive-compulsive behavior, for altering macronutrient preferences, and for reducing craving of substances, particularly substances of abuse such as alcohol, tobacco, opiates and other narcotics.

Compounds of formula I wherein $R_{5-9}$ are all H are particularly useful for partial appetite suppression. These compounds provide partial suppression (where food intake is 20–70% of control) over a wide dose range, in contrast to full anorectic agents which provide large suppression ($\leq 80\%$) at effective dosages, and provide partial suppression over a very narrow range. As it is impractical to titrate the dosage of a full anorectic agent for each patient to achieve a particular partial appetite suppression, the method of the invention for partial appetite suppression is distinct and advantageous.

C. Examples

The examples presented below are provided as a further guide to the practitioner of ordinary skill in the art, and are not to be construed as limiting the invention in any way.

EXAMPLE 1

(Preparation of Compounds)

(A) L-1-Carboxy-1,2,3,4-tetrahydro-beta-carboline hydrochloride was prepared as follows:

L-Tryptophan benzyl ester hydrochloride (3.308 g, 10 mmol, obtained from Bachem) was suspended in 0.05 N $H_2SO_4$ (18.8 mL) with stirring, and 37% formaldehyde (0.938 mL) was added. The reaction mixture cleared, followed by crystallization of the product. Stirring was continued for 24 hours, and the product filtered off, and dried over $P_2O_5$ One gram of crude material was crystallized from ethanol:water, by dissolving in 20 mL EtOH with gentle warming, adding 30 mL water, and evaporating the mixture to $\frac{2}{3}$ volume. The precipitated material was filtered off and discarded. The mother liquor was further evaporated to $\frac{1}{4}$ volume, and was refrigerated overnight. The product crystals were filtered and dried over $P_2O_5$.

Calculated for $C_{19}H_{18}O_2N_2$ (%): C-66.57; H-5.59; N-8.08; 0-9.33; Cl-10.34. Found: C-66.45; H-5.45; N-8.08; 0-9.67; Cl-10.18.

(B) D,L-1-Carboxy-1,2,3,4-tetrahydro-beta-carboline was prepared as follows:

A solution of 110 mmol glyoxylic acid monohydrate (10.1 g, obtained from Sigma) in 23 mL water was added to 100 mmol tryptamine HCl (19.7 g, obtained from Sigma) in 310 mL water. The stirred mixture was brought to pH 4 with 10 N NaOH and maintained at ambient temperature for 1 hr. The precipitated solid was filtered, washed with 100 mL water, and recrystallized from $EtOH/H_2O$ to provide D,L-1-carboxy-1,2,3,4-tetrahydro-beta-carboline ($R_1$=COOH; $R_{2-9}$=H).

Calculated for $C_{12}H_{12}N_2O_2$ (%): C-66.65; H-5.59; N-12.95; 0-14.80. Found: C-66.51; H-5.58; N-12.88; O-15.01.

(C) 2-Acetyl-1,2,3,4-tetrahydro-beta-carboline was prepared as follows:

A solution of 10 mmol D,L-1,2,3,4-tetrahydrobeta-carboline-1-carboxylic acid (2.16 g) in 30 mL 2.5 N hydrochloric acid was boiled for 1 hr to provide 1,2,3,4-tetrahydro-beta-carboline. The product precipitated on cooling, and was filtered, washed with 5 mL water, and dried under vacuum. One gram of the product was dissolved in a minimum amount of water and brought to pH 12 with 10 N NaOH. The precipitated free base was centrifuged, washed with water (2×30 mL) and dried under vacuum. The product was then dissolved in a minimum of ethyl acetate, and pyridine (3 mL, 37 mmol) and acetic anhydride (1.5 mL, 16 mmol) were added. After 30 minutes, the mixture was dried, and the resulting 2-acetyl-1,2,3,4-tetrahydro-beta-carboline was crystallized from acetone ($R_1$=$R_{3-9}$=H; $R_2$=COMe).

Calculated for $C_{13}H_{14}N_2O$ (%): C-72.87; H-6.59; N-13.07; 0-7.47. Found: C-72.88; H-6.47; N-12.94; 0-7.75.

(D) 9-(1-pentyl)-1,2,3,4-tetrahydro-beta-carboline hydrochloride was prepared as follows:

Under a nitrogen atmosphere, 8.0 mmol 2-acetyl-1,2,3,4-tetrahydro-beta-carboline (1.71 g) was dissolved in 40 mL dry dimethylformamide (DMF). The solution was stirred over ice, and NaH (2 g) was added under $N_2$. The suspension was stirred for 1 hour, and then 1-bromopentane (9.2 mmol, 1.14 mL, 1.39 g) was added slowly to the cooled suspension. After a further 2 hours of stirring at ambient temperature, the mixture was filtered and the filtrate added to 320 mL 0.1 N HCl. Crude 2-acetyl-9-(1-pentyl)-1,2,3,4-tetrahydro-beta-carboline separated as an oil. The oil was collected by centrifugation, washed with water, and dried over anhydrous $MgSO_4$. ($R_1$=$R_{3-8}$=H; $R_2$=Ac; $R_9$=$C_5H_{11}$)

A portion of the crude 2-acetyl-9-(1-pentyl)-1,2,3,4-tetrahydro-beta-carboline (1.7 g) was heated at reflux for 4.5 hours in 2 N NaOH (50 mL) in methanol:water (2:3, v/v). The methanol was removed by evaporation under vacuum, and the crude 9-(1-pentyl)-1,2,3,4-tetrahydro-beta-carboline free base was extracted into chloroform. This extract was dried over anhydrous $MgS_4$, filtered, and the filtrate evaporated under vacuum. The hydrochloride salt was prepared by passing dry HCl through a solution of the crude free base in diethyl ether. The resulting precipitate was filtered and recrystallized from acetonitrile to yield pure 9-(1-pentyl)-1,2,3,4-tetrahydro-beta-carboline ($R_{1-8}$=H; $R_9$=$C_5H_{11}$).

Calculated for (%): $C_{16}H_{28}N_2Cl$ (%): C-68.92; H-8.32; N-10.05; Cl-12.72. Found: C-69.20; H-8.51; N-9.95; Cl-12.58.

(E) 5-Methyl-1,2,3,4-tetrahydro-betacarboline hydrochloride was prepared as follows:

A suspension of 4-methyltryptophan (1.14 g, 5.2 mmol, Sigma) in diphenylmethane (45 mL) was heated at reflux until complete solution was obtained. The solution was then mixed with 45 mL water and 45 mL ethyl acetate, and the pH brought to 1 or lower with concentrated HCl. The mixture was vortexed vigorously for 30 seconds, and centrifuged to provide three layers. The middle (aqueous) layer was washed with ethyl acetate, and adjusted to pH 10 or higher with 10 N NaOH. The resulting white precipitate was extracted into ethyl acetate, and the extract evaporated to dryness under vacuum, to yield crude 4-methyltryptamine base. The crude base was dissolved and acidified in 50 mL EtOH containing 6 mmol 6 N HCl, and the resulting 4-methyltryptamine hydrochloride was crystallized from solution.

5-Methyl-1,2,3,4-tetrahydro-beta-carboline hydrochloride was prepared following the procedure described in parts B and C above, substituting 4-methyltryptamine hydrochloride for tryptamine hydrochloride. The product was recrystallized from EtOH.

Calculated for $C_{12}H_{15}N_2Cl$ (%): C-64.72; H-6.79; N-12.58; Cl-15.92. Found: C-64.48; H-6.81; N-12.33; Cl-15.55.

(F) 6-Methyl-1,2,3,4-tetrahydro-betacarboline hydrochloride was prepared as follows:

5-Methyltryptamine hydrochloride (Sigma) was condensed with glyoxylic acid as described in part B above, and decarboxylated according to the procedure described in part C. The product, 6-methyl-1,2,3,4-tetrahydro-beta-carboline hydrochloride was recrystallized from ethanol:water ($R_{1-5}=R_{7-9}=H$; $R_6=Me$). Calculated for $C_{12}H_{15}N_2Cl$ (%): C-64.72; H-6.79; N-12.58; Cl-15.92. Found: C-64.51; H-6.76; N-12.42; Cl-15.79.

(G) 7-Fluoro-1,2,3,4-tetrahydro-beta-carboline hydrochloride was prepared as follows:

6-Fluorotryptamine hydrochloride (Sigma) was condensed with glyoxylic acid as described in part B, and decarboxylated according to part C. The product, 7-fluoro-1,2,3,4-tetrahydro-beta-carboline hydrochloride was recrystallized from ethanol:water ($R_{1-6}=R_{8-9}=H$; $R_7$32 F).

Calculated for $C_{11}H_{12}N_2FCl$ (%): C-58.28; H-5.34; N-12.36; F-8.38; Cl-15.64. Found: C-58.50; H-5.29; N-12.43; F-8.11; Cl-15.35.

(H) 8-Methyl-1,2,3,4-tetrahydro-betacarboline hydrochloride was prepared as follows:

7-Methyltryptamine (free base, Sigma) was dissolved in aqueous hydrochloric acid and condensed with glyoxylic acid as described in part B. The product was decarboxylated according to part C to yield 8-methyl-1,2,3,4-tetrahydro-beta-carboline hydrochloride, which was recrystallized from ethanol:water $R_{1-7}=R_9=H$; $R_8=Me$).

Calculated for $C_{12}H_{15}N_2Cl$(%): C-64.72; H-6.79; N-12.58; Cl-15.92. Found: C-64.61; H-6.86; N-12.61; Cl-15.48.

EXAMPLE 2

(Reduction of Food Intake) Dose ranging studies showed that compounds of formula I significantly reduced food intake when administered parenterally to rats in amounts appreciably lower than 25 mg/Kg.

Adult male rats weighing between 250 and 300 g were acclimated to laboratory conditions for a period of 4–5 days, during which they were allowed unrestricted access to food (Ralston-Purina #5001M) and water. All animals were housed in individual cages. The animal facility was maintained on a 12:12 hr light-dark schedule at 22° C.

Fasted animals were sorted into groups of 10–12 each by weight and baseline food intake. Each was then given saline containing 0–32 mg/Kg of a compound of the invention (or THBC) by intraperitoneal injection. After 20 minutes, animals were allowed access to food and water. Cumulative food intake was measured at 1 hour post-injection. Doses as low as 4 mg/Kg significantly reduced food consumption (Table I).

In the examples herein, compounds were administered parenterally. In clinical usage as an anorectic agent in mammals, particularly humans, the oral, intranasal, or transdermal routes of administration would be preferred. In the case of intraperitoneal administration in rodents, amounts as low as about 1.5 mg/Kg of body weight have been shown to achieve effective significant appetite suppression.

TABLE I
(Reduction of Food Intake)

| Compound | Dose (mg/Kg) | 1 Hr Food Intake (g, mean + sem) | p |
|---|---|---|---|
| THBC (HCl) | 0 | 5.13 ± 0.51 | NA |
|  | 5.0 | 4.44 ± 0.36 | <0.14 |
|  | 10.0 | 3.70 ± 0.18 | <0.01 |
|  | 15.0 | 2.63 ± 0.21 | <0.00021 |
|  | 25.0 | 1.10 ± 0.12 | $<2.9 \times 10^{-6}$ |
| $R_6$ = OMe (HCl) | 0 | 5.88 ± 0.56 | NA |
|  | 5.0 | 5.08 ± 0.33 | <0.12 |
|  | 10.0 | 4.45 ± 0.20 | <0.015 |
|  | 15.0 | 2.88 ± 0.31 | <0.0001 |
|  | 25.0 | 1.74 ± 0.26 | $<3.4 \times 10^{-6}$ |
| $R_6$ = F (HCl) | 0 | 5.53 ± 0.49 | NA |
|  | 5.0 | 4.20 ± 0.27 | <0.015 |
|  | 10.0 | 2.29 ± 0.21 | $<1.0 \times 10^{-5}$ |
|  | 15.0 | 1.89 ± 0.14 | $<3.5 \times 10^{-6}$ |
|  | 25.0 | 0.73 ± 0.15 | $<1.8 \times 10^{-7}$ |
| $R_7$ = F (HCl) | 0 | 4.99 ± 0.40 | NA |
|  | 5.0 | 3.99 ± 0.57 | <0.083 |
|  | 10.0 | 2.78 ± 0.27 | $<9.1 \times 10^{-5}$ |
|  | 25.0 | 0.50 ± 0.12 | $<7.4 \times 10^{-8}$ |
| $R_1$ = Me (HCl) | 0 | 5.33 ± 0.39 | NA |
|  | 5.0 | 5.16 ± 0.51 | <0.39 |
|  | 10.0 | 3.95 ± 0.26 | <0.0038 |
|  | 25.0 | 2.36 ± 0.20 | $<2.3 \times 10^{-6}$ |
| $R_6$ = Cl | 0 | 4.12 ± 0.44 | NA |
|  | 5.0 | 3.75 ± 0.39 | <0.27 |
|  | 10.0 | 2.42 ± 0.24 | <0.0016 |
|  | 25.0 | 0.58 ± 0.22 | $<9.3 \times 10^{-7}$ |
| $R_6$ = Cl (HCl) | 0 | 5.85 ± 0.41 | NA |
|  | 4.0 | 3.68 ± 0.42 | <0.00076 |
|  | 8.0 | 2.69 ± 0.17 | $<5.4 \times 10^{-6}$ |
|  | 16.0 | 2.22 ± 0.22 | $<8.5 \times 10^{-7}$ |
|  | 32.0 | 0.29 ± 0.14 | $<2.6 \times 10^{-8}$ |
| $R_2$ = Me (HCl) | 0 | 4.69 ± 0.54 | NA |
|  | 5.0 | 4.66 ± 0.33 | <0.48 |
|  | 10.0 | 3.73 ± 0.29 | <0.068 |
|  | 25.0 | 2.27 ± 0.24 | <0.00046 |
| $R_8$ = Me (HCl) | 0 | 5.28 ± 0.66 | NA |
|  | 5.0 | 4.42 ± 0.42 | <0.14 |
|  | 10.0 | 3.30 ± 0.23 | <0.0075 |
|  | 25.0 | 0.56 ± 0.33 | $<6.0 \times 10^{-6}$ |
| $R_6$ = Me (HCl) | 0 | 4.50 ± 0.42 | NA |
|  | 5.0 | 2.69 ± 0.22 | <0.00073 |
|  | 10.0 | 1.53 ± 0.24 | $<4.5 \times 10^{-6}$ |
|  | 25.0 | 0.08 ± 0.02 | $<2.3 \times 10^{-7}$ |
| $R_3$ = Et (HCl) | 0 | 4.86 ± 0.52 | NA |
|  | 5.0 | 5.42 ± 0.56 | <0.24 |
|  | 10.0 | 3.66 ± 0.40 | <0.041 |
|  | 25.0 | 1.47 ± 0.21 | $<1.2 \times 10^{-5}$ |
| $R_3$ = COOH (HCl) | 0 | 6.47 ± 0.33 | NA |
|  | 4 | 4.72 ± 0.45 | <0.0029 |
|  | 8 | 2.57 ± 0.32 | $<5.4 \times 10^{-8}$ |
|  | 16 | 2.31 ± 0.23 | $<3.0 \times 10^{-9}$ |
|  | 32 | 2.11 ± 0.25 | $<2.2 \times 10^{-9}$ |
| $R_3$ = COOH, $R_6$ = OH | 0 | 5.18 ± 0.44 | NA |
|  | 4.0 | 6.00 ± 0.31 | <0.074 |
|  | 8.0 | 4.89 ± 0.38 | <0.31 |
|  | 16.0 | 3.12 ± 0.48 | <0.0027 |
|  | 32.0 | 1.57 ± 0.31 | $<1.5 \times 10^{-6}$ |
| $R_2$ = Ac | 0 | 7.19 ± 0.44 | NA |
|  | 4.0 | 5.21 ± 0.33 | <0.0011 |
|  | 8.0 | 3.27 ± 0.34 | $<7.1 \times 10^{-7}$ |
|  | 16.0 | 2.85 ± 0.19 | $<5.4 \times 10^{-7}$ |
|  | 32.0 | 2.80 ± 0.20 | $<3.0 \times 10^{-7}$ |
| $R_5$ = Me (HCl) | 0 | 6.78 ± 0.50 | NA |
|  | 4.0 | 3.76 ± 0.32 | $<3.8 \times 10^{-5}$ |
|  | 8.0 | 3.22 ± 0.42 | $<1.6 \times 10^{-5}$ |

TABLE I-continued (Reduction of Food Intake)

| Compound | Dose (mg/Kg) | 1 Hr Food Intake (g, mean + sem) | p |
|---|---|---|---|
| | 16.0 | 2.22 ± 0.22 | $<1.2 \times 10^{-6}$ |
| | 32.0 | 0.10 ± 0.05 | $<1.6 \times 10^{-7}$ |
| $R_9$ = CHO | 0 | 4.44 ± 0.42 | NA |
| | 4.0 | 4.35 ± 0.41 | <0.44 |
| | 8.0 | 3.96 ± 0.14 | <0.15 |
| | 16.0 | 3.23 ± 0.25 | <0.012 |
| | 32.0 | 1.03 ± 0.35 | $<3.6 \times 10^{-6}$ |
| $R_9$ = Bz (HCl) | 0 | 5.91 ± 0.33 | NA |
| | 4.0 | 4.34 ± 0.53 | <0.011 |
| | 8.0 | 2.36 ± 0.18 | $<8.2 \times 10^{-8}$ |
| | 16.0 | 0.51 ± 0.18 | $<3.9 \times 10^{-10}$ |
| | 32.0 | 0.10 ± 0.02 | $<1.3 \times 10^{-8}$ |
| $R_9$ = Et (HCl) | 0 | 6.02 ± 0.46 | NA |
| | 4.0 | 4.01 ± 0.37 | <0.0015 |
| | 8.0 | 3.03 ± 0.26 | $<2.8 \times 10^{-5}$ |
| | 16.0 | 2.65 ± 0.23 | $<9.1 \times 10^{-6}$ |
| | 32.0 | 0.13 ± 0.07 | $<2.4 \times 10^{-7}$ |
| $R_6$ = Me, $R_9$ = Pent (HCl) | 0 | 6.34 ± 0.44 | NA |
| | 4.0 | 3.72 ± 0.22 | $<6.5 \times 10^{-5}$ |
| | 8.0 | 2.46 ± 0.11 | $<3.1 \times 10^{-6}$ |
| | 16.0 | 0.64 ± 0.14 | $<4.3 \times 10^{-8}$ |
| | 32.0 | 0.26 ± 0.03 | $<1.1 \times 10^{-7}$ |
| $R_9$ = Pent (HCl) | 0 | 5.18 ± 0.44 | NA |
| | 4.0 | 2.89 ± 0.37 | <0.00045 |
| | 8.0 | 2.27 ± 0.17 | $<2.4 \times 10^{-5}$ |
| | 16.0 | 0.93 ± 0.21 | $<4.4 \times 10^{-7}$ |
| | 32.0 | 0.01 ± 0.01 | $<4.5 \times 10^{-6}$ |
| $R_3$ = COOBz (HCl) | 0 | 5.74 ± 0.46 | NA |
| | 4.0 | 5.06 ± 0.49 | <0.16 |
| | 8.0 | 3.81 ± 0.45 | <0.004 |
| | 16.0 | 2.55 ± 0.21 | $<2.0 \times 10^{-5}$ |
| | 32.0 | 2.86 ± 0.27 | $<2.2 \times 10^{-5}$ |
| $R_1$ = Me, $R_3$ = COOH, $R_9$ = Me | 0 | 4.99 ± 0.59 | NA |
| | 4.0 | 4.41 ± 0.44 | <0.23 |
| | 8.0 | 2.94 ± 0.22 | <0.0039 |
| | 16.0 | 3.13 ± 0.41 | <0.0092 |
| | 32.0 | 2.69 ± 0.45 | <0.0031 |
| $R_1$ = COOH | 0 | 4.84 ± 0.53 | NA |
| | 4.0 | 3.74 ± 0.25 | <0.042 |
| | 8.0 | 3.21 ± 0.30 | <0.0075 |
| | 16.0 | 2.89 ± 0.13 | <0.0025 |
| | 32.0 | 1.83 ± 0.14 | <0.00013 |
| $R_2$ = Ac, $R_9$ = Bz | 0 | 4.82 ± 0.56 | NA |
| | 4.0 | 4.00 ± 0.56 | <0.16 |
| | 8.0 | 3.18 ± 0.28 | <0.01 |
| | 16.0 | 2.04 ± 0.19 | <0.00032 |
| | 32.0 | 0.82 ± 0.14 | $<2.0 \times 10^{-5}$ |
| $R_3$ = COOH (D isomer) | 0 | 5.50 ± 0.43 | NA |
| | 4.0 | 5.48 ± 0.29 | <0.48 |
| | 8.0 | 5.99 ± 0.30 | <0.18 |
| | 16.0 | 4.58 ± 0.66 | <0.13 |
| | 32.0 | 2.34 ± 0.40 | $<2.8 \times 10^{-5}$ |
| $R_1$ = COOH, $R_3$ = COOMe (HCl) | 0 | 6.64 ± 0.33 | NA |
| | 4.0 | 5.50 ± 0.65 | <0.072 |
| | 8.0 | 5.90 ± 0.61 | <0.15 |
| | 16.0 | 4.53 ± 0.53 | <0.0016 |
| | 32.0 | 4.22 ± 0.27 | $<1.2 \times 10^{-5}$ |
| $R_2$ = Suc | 0 | 5.05 ± 0.45 | NA |
| | 4.0 | 5.65 ± 0.37 | <0.16 |
| | 8.0 | 5.80 ± 0.47 | <0.13 |
| | 16.0 | 5.85 ± 0.45 | <0.11 |
| | 32.0 | 2.45 ± 0.29 | $<6.8 \times 10^{-5}$ |

$R_{1-9}$ = H unless otherwise specified. Me = methyl; Et = ethyl; Ac = acetyl; Bz = benzyl; Pent = pentyl; Suc = succinyl. All compounds are racemic unless otherwise specified. p values were computed by two-tailed Students t-test.

EXAMPLE 3

(Dose Response Characteristics)

A number of compounds of the invention exhibit dose-response characteristics which are qualitatively different from those of THBC. Unlike THBC, several compounds of formula I will not depress feeding behavior to zero over a comparatively large concentration range. This feature is termed "partial suppression" of feeding behavior, and greatly increases the margin of safety, as overuse of the compounds will not result in fatal anorexia.

Reduction in food intake over one hour was measured versus dose per unit body weight for THBC, and for 2-acetyl-THBC ($R_2$=C(O)CH$_3$), D,L-3-carboxy-THBC ($R_3$=COOH), D,L-1-carboxy-THBC ($R_1$=COOH), and D,L-3-carbobenzyloxy-THBC ($R_3$=COOCH$_2$C$_6$H$_5$).

Figure 2:
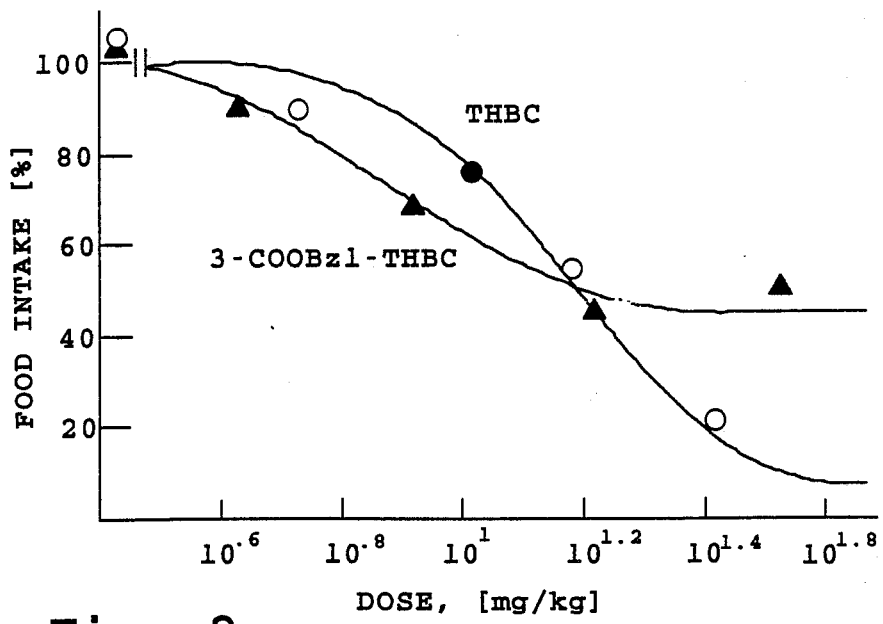
Figure 3:
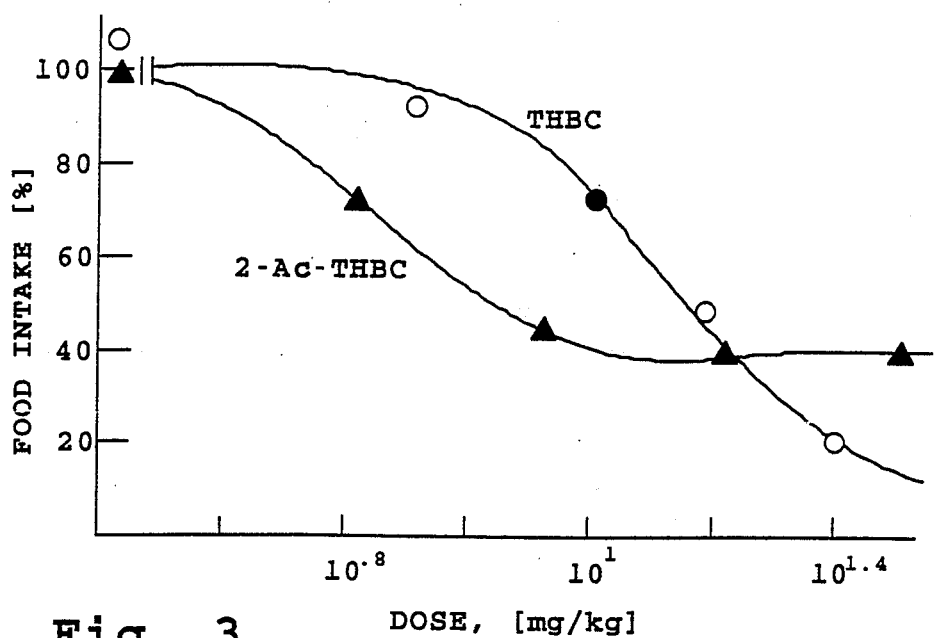
Figure 4:
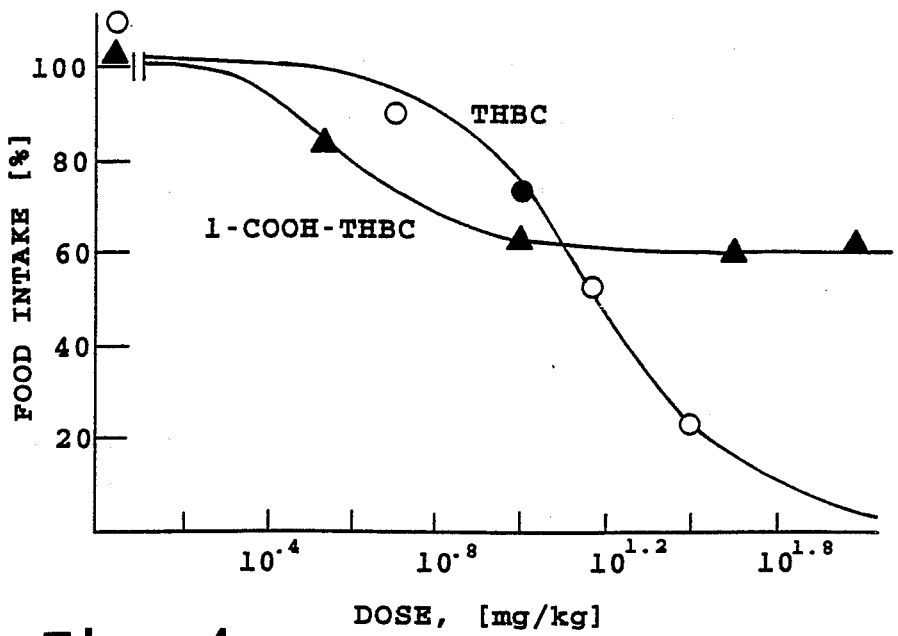

The results are shown in FIGS. 1-4. FIG. 1 compares D,L-3-carboxy-THBC ($R_3$=COOH) with THBC. FIG. 2 compares D,L-3-carbobenzyloxy-THBC ($R_3$=COOCH$_2$C$_6$H$_5$) with THBC. FIG. 3 compares 2-acetyl-THBC ($R_2$=C(O)CH$_3$) with THBC. FIG. 4 compares D,L-1-carboxy-THBC carboxy-THBC ($R_1$=COOH) with THBC. (Note that the scales vary from figure to figure.) The results demonstrated that THBC effected little feeding depression at low dosage, but relatively complete feeding depression at higher dosage, with a comparatively narrow range of concentration in the transition region. In contrast, each of the compounds tested demonstrated moderate feeding depression over a broad dosage range, beginning at dosages lower than required for THBC, and extending past dosages at which THBC caused complete feeding cessation.

EXAMPLE 4

(Alteration of Macronutrient Preference)

This Example demonstrates alteration of macronutrient preference in rats.

Sixty adult male rats (Sprague-Dawley, 225-300 g) are acclimated to laboratory conditions for a period of 10 days, during which they are allowed unrestricted access to food (Ralston-Purina #5001M) and water. All subjects are housed in individual cages, and the animal facility is maintained on a 12:12 hour light:dark cycle at 24°-27° C.

Animals are assigned to 6 groups (10 per group), then allowed to consume, ad libitum, one of two iso-nitrogenous test diets containing either 75% or 25% carbohydrate. After 3 days, food jars are removed. After an additional 24 hours, rats are administered either saline or a compound of formula I (1.5 or 3.0 mg/Kg body weight), then given immediate access to the test diets. The cumulative amount in grams (mean±SEM) of each diet consumed by the experimental and control groups during the subsequent 2-hour period is recorded.

The results indicate that animals receiving a compound of the invention consume significantly less of the high carbohydrate diet than do controls, but consume equivalent quantities of the low carbohydrate diet. Thus, compounds of the invention selectively suppress carbohydrate cravings when administered at doses lower than the dosage effective for global reduction in appetite. This demonstrates the utility of the present invention as a method for reducing substance cravings per se, insofar as food cravings model clinical syndromes in which there is excessive preoccupation with, or urges for, specific habituating substances (Glassman et al., Science (1984) 226:864). Accordingly, this Example may be taken as evidencing efficacy in the treatment of alcohol, tobacco, or drug (particularly opiate) addiction.

EXAMPLE 5

(Formulations)

(A) A representative capsule formulation is prepared as follows:

| Compound | 50.0 mg |
|---|---|
| starch | 3.0 mg |
| magnesium stearate | 3.0 mg |
| lactose | 110.0 mg |
| polyvinylpyrrolidone | 3.0 mg |

The compound of formula I, starch, magnesium stearate, lactose, and polyvinylpyrrolidone are granulated in methanol, dried, and loaded into capsules. Alternatively, the mixture may be tableted by standard methods.

(B) An oral suspension is prepared as follows:

| Compound | 60.0 mg |
|---|---|
| fumaric acid | 0.5 g |
| NaCl | 2.0 g |
| methyl paraben | 0.1 g |
| granulated sugar | 25.5 2 |
| sorbitol (70% aq) | 12.85 g |
| Veegum K | 1.0 g |
| flavorings | 0.035 mL |
| colorings | 0.5 mg |
| distilled water qs | 100.0 mL |

The components are mixed together and stored in a sealed vessel.

(D) A formulation suitable for parenteral administration is prepared as follows:

| Compound | 40.0 mg |
|---|---|
| KH$_2$PO$_4$ buffer (0.4M) | 2.0 mL |
| KOH (1N) qs | pH 7.0 |
| water qs | 20.0 mL |

The components are mixed together and stored under sterile conditions.

The foregoing is offered primarily for purposes of illustration. It will be readily apparent to those skilled in the art that numerous variations, modifications and substituents, in the materials and methods described herein may be made without departing from the spirit and scope of the invention.

What is claimed:

1. A method for altering macronutrient preference in a mammal, which comprises:
    administering to a mammal in need thereof an appetite altering amount of a compound selected from the group consisting of:
    6-methyl-1,2,3,4-tetrahydro-[beta]β-carboline,
    6-methyl-9-pentyl-1,2,3,4-tetrahydro-[beta]β-carboline,
    3-carboxy-1,2,3,4-tetrahydro-[beta]β-carboline,
    1-carboxy-1,2,3,4-tetrahydro-[beta]β-carboline,
    2-acetyl-1,2,3,4-tetrahydro-[beta]β-carboline,
    5-methyl-1,2,3,4-tetrahydro[beta]β-carboline,
    9-benzyl-1,2,3,4-tetrahydro-[beta]β-carboline,
    9-ethyl-1,2,3,4-tetrahydro-[beta]β-carboline,
    3-carbobenzyloxy-1,2,3,4-tetrahydro-[beta]β-carboline,
    1-carboxamido-1,2,3,4-tetrahydro-[beta]β-carboline,
    3-carboxamido-1,2,3,4-tetrahydro-[beta]β-carboline, and
    9-pentyl-1,2,3,4-tetrahydro-[beta]β-carboline.

2. A composition for altering macronutrient preference in a mammal, which comprises:
    a pharmaceutically-acceptable excipient; and
    an appetite altering amount of a compound selected from the group consisting of:
    6-methyl-1,2,3,4-tetrahydro-[beta]β-carboline,
    6-methyl-9-pentyl-1,2,3,4-tetrahydro-[beta]β-carboline,
    3-carboxy-1,2,3,4-tetrahydro-[beta]β-carboline,
    1-carboxy-1,2,3,4-tetrahydro-[beta]β-carboline,
    2-acetyl-1,2,3,4-tetrahydro-[beta]β-carboline,
    5-methyl-1,2,3,4-tetrahydro-[beta]β-carboline,
    9-benzyl-1,2,3,4-tetrahydro-[beta]β-carboline,
    9-ethyl-1,2,3,4-tetrahydro-[beta]β-carboline,
    3-carbobenzyloxy-1,2,3,4-tetrahydro-[beta]β-carboline,
    1-carboxamido-1, 2,3,4-tetrahydro-[beta]β-carboline,
    3-carboxamido-1,2,3,4-tetrahydro-[beta]β-carboline, and
    9-pentyl-1,2,3,4-tetrahdyro-[beta]β-carboline.

* * * * *